United States Patent [19]

Gorman et al.

[11] 4,420,484
[45] Dec. 13, 1983

[54] BASIC AMINO OR AMMONIUM ANTIMICROBIAL AGENT-POLYETHYLENE GLYCOL ESTER SURFACTANT-BETAINE AND/OR AMINE OXIDE SURFACTANT COMPOSITIONS AND METHOD OF USE THEROF

[75] Inventors: William G. Gorman, East Greenbush; Karl F. Popp, Schodack Landing, both of N.Y.

[73] Assignee: Sterling Drug Inc., New York, N.Y.

[21] Appl. No.: 320,754

[22] Filed: Nov. 12, 1981

Related U.S. Application Data

[63] Continuation-in-part of Ser. No. 245,089, Mar. 18, 1981, abandoned, which is a continuation-in-part of Ser. No. 158,737, Jun. 12, 1980, abandoned, which is a continuation-in-part of Ser. No. 65,885, Aug. 13, 1979, abandoned.

[51] Int. Cl.$^3$ ............................................. A61K 31/55
[52] U.S. Cl. ................................. 424/326; 424/263; 424/329
[58] Field of Search ................. 424/326, 329, 263

[56] References Cited

U.S. PATENT DOCUMENTS

| | | | |
|---|---|---|---|
| 2,684,924 | 7/1954 | Rose et al. | 167/30 |
| 2,990,425 | 6/1961 | Senior | 260/501 |
| 3,468,898 | 9/1969 | Cutler et al. | 260/301 |
| 3,775,477 | 11/1973 | Diana | 260/558 |
| 3,855,140 | 12/1974 | Billany et al. | 252/106 |
| 3,867,454 | 2/1975 | Diana et al. | 260/570.5 P |
| 3,940,441 | 2/1976 | Surrey | 260/562 B |
| 4,022,834 | 5/1977 | Gundersen | 260/564 B |
| 4,045,483 | 8/1977 | Cutler et al. | 260/552 R |
| 4,053,636 | 10/1977 | Eustis et al. | 424/326 |
| 4,140,860 | 2/1979 | Diana et al. | 560/29 |

FOREIGN PATENT DOCUMENTS 1533952 of 0000 United Kingdom .

OTHER PUBLICATIONS

The Merck Index, Ninth Edition, Merck & Co., Inc., 1976:Monographs 224, 1059, 1078, 1987, 2060 and 2874.
Disinfection, Sterilization and Preservation (Block), 2nd Edition, Lea & Febiger, 1977, pp. 325-360.
Nonionic Surfactants (Schick), Marcel Dekker Inc., 1967, pp. 142-174.
AROMOX Amine Oxides, Armak Co. Bulletin No. 74-21, 1974.

*Primary Examiner*—Leonard Schenkman
*Attorney, Agent, or Firm*—Theodore C. Miller; Paul E. Dupont; B. Woodrow Wyatt

[57] ABSTRACT

Basic amino or ammonium antimicrobial agent (especially bisbiguanide, quaternary ammonium salt and bispyridine)-polyethylene glycol ester surfactant-betaine and/or amine oxide surfactant antimicrobial skin cleansing compositions and method of use thereof are disclosed.

31 Claims, No Drawings

BASIC AMINO OR AMMONIUM ANTIMICROBIAL AGENT-POLYETHYLENE GLYCOL ESTER SURFACTANT-BETAINE AND/OR AMINE OXIDE SURFACTANT COMPOSITIONS AND METHOD OF USE THEROF

CROSS-REFERENCE TO RELATED APPLICATIONS

This application is a continuation-in-part of our copending application Ser. No. 245,089 filed Mar. 18, 1981 now abandoned, which is a continuation-in-part of our copending application Ser. No. 158,737 filed June 12, 1980 and now abandoned, which is a continuation-in-part of our copending application Ser. No. 65,885 filed Aug. 13, 1979 and now abandoned.

BACKGROUND OF THE INVENTION

1. Field of the Invention

The invention relates to basic amino or ammonium antimicrobial agent (especially bisbiguanide, quaternary ammonium salt and bispyridine)-polyethylene glycol ester surfactantbetaine and/or amine oxide surfactants antimicrobial skin cleansing compositions and method of use thereof.

2. Description of the Prior Art

Antimicrobial aryl bisbiguanides (U.S. Pat. No. 2,684,924; U.S. Pat. No. 4,053,636) including chlorhexidine (The Merck Index, Ninth Edition, 1976, monograph 2060) and chlorhexidine digluconate salt (U.S. Pat. No. 2,990,425) are known. U.S. Pat. No. 3,855,140 describes polyoxyethylene-polyoxypropylene block copolymer cleansing compositions of certain chlorhexidine salts including chlorhexidine digluconate salt. Antimicrobial alkyl bisbiguanides (U.S. Pat. No. 3,468,898) including alexidine (The Merck Index, ibid., monograph 224) and aqueous compositions thereof with "a compatible surfactant or surfactant mixture selected from the cationic, non-ionic and amphoteric surfactants" (Belgian Pat. No. 862,808) and cycloalkyl bisbiguanides (U.S. Pat. No. 4,022,834) are also known.

The quaternary ammonium disinfectants (A. N. Petrocci, Disinfection, Sterilization, and Preservation, 2nd Edition, Seymour S. Block, Editor, Lea & Febiger, Philadelphia, 1977, pp. 325-347) are a well-known class of antimicrobial agents. Particularly well-known examples are benzalkonium chloride (The Merck Index, ibid., monograph 1059), benzethonium chloride (ibid., monograph 1078), cetylpyridinium chloride (ibid., monograph 1987), dequalinium chloride (ibid., monograph 2874) and N-myristyl-N-methylmorpholinium methyl sulfate.

Antimicrobial bispyridines and compositions thereof "with any compatible, pharmaceutically acceptable surfactant, preferably a non-ionic surfactant, such as the polyoxyethylene polyoxypropylene copolymers . . . amine oxides, such as stearyl dimethyl amine oxide . . . or with mixtures of these" are described by British Pat. No. 1,533,952.

Numerous other basic amino and ammonium antimicrobial agents are described by the prior art, as illustrated by the following examples. Amidinoureas are described by U.S. Pat. No. 4,045,483. U.S. Pat. No. 3,940,441 describes bisphenoxybenzyldiamines. U.S. Pat. No. 3,775,477, U.S. Pat. No. 3,867,454 and U.S. Pat. No. 4,140,860 describe dioldiamines.

The polyethylene glycol or polyoxyethylene esters of fatty acids are a known class of surfactants (W. B. Satkowski, S. K. Huang and R. L. Liss in Nonionic Surfactants, Martin J. Schick, Editor, Marcel Dekker, Inc., New York, 1967, pp. 142-174) of the nonionic type, members of which are listed by trade name (McCutcheon's Detergents & Emulsifiers, North American Edition, McCutcheon Division, MC Publishing Co., 175 Rock Road, Glen Rock, NJ 07452, 1977) and generic name (CTFA Cosmetic Ingredient Dictionary, Second Edition, The Cosmetic, Toiletry and Fragrance Association, Inc., 1133 Fifteenth Street, N.W., Washington, D.C. 20005, 1977).

The betaine surfactants are also known and are of the amphoteric type (McCutcheon's Detergents & Emulsifiers, ibid.; CTFA Cosmetic Ingredient Dictionary, ibid.). Members of the class have antimicrobial properties as well as surfactant properties (Seymour S. Block, Disinfection, Sterilization, and Preservation, ibid., pp. 348-360).

The amine oxide detergents are also known and are of the nonionic type (AROMOX Amine Oxides, Product Data Bulletin No. 74-21 of Armak Company, Box 1805, Chicago, Ill., 60690, 1974; McCutcheon's Detergents and Emulsifiers, ibid., CTFA Cosmetic Ingredient Dictionary, ibid.).

There is a need for antimicrobial skin cleansing compositions having better sudsing ability than the compositions of the prior art, especially those of above-cited U.S. Pat. No. 3,855,140. The presently described and claimed invention is designed to meet this need.

SUMMARY OF THE INVENTION

In a composition of matter aspect the invention is an antimicrobial skin cleansing composition consisting essentially of (A) an antimicrobially effective amount of one or more antimicrobial agents selected from the group consisting of (a) a compound having the structural formula Formula I

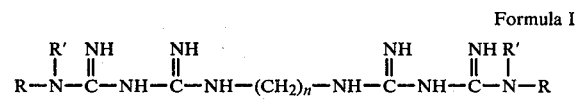

wherein R taken alone is phenyl substituted by alkyl, alkoxy, nitro or halo, p-(2,2-dichlorocyclopropyl)phenyl, alkyl having from 6 to 16 carbon atoms, cycloalkyl or polycyclic alkyl having more than 6 carbon atoms or lower-alkyl-cycloalkyl or cycloalkyl-lower-alkyl having from 1 to 4 carbons in lower alkyl; R' taken alone is hydrogen; R and R' taken together are 3-azabicyclo(3,2,2)nonyl; and n is an integer from 3 to 9; or a pharmaceutically acceptable salt thereof;

(b) a compound having the structural formula

Formula II

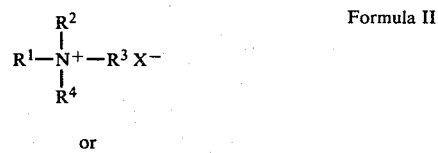

or

-continued

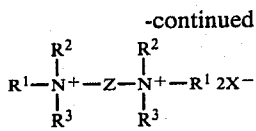
Formula III wherein $R^1$ is long-chain alkyl or aralkyl; $R^2$ is short-chain alkyl, long-chain alkyl or aralkyl, benzyl or part of an aromatic system or non-aromatic system; $R^3$ and $R^4$ are short-chain alkyl or part of an aromatic ring system or non-aromatic ring system; Z is a carbonhydrogen chain; and X is a pharmaceutically acceptable anion; and (c) a compound having the structural formula

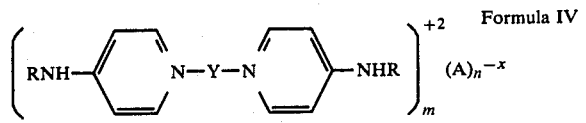
Formula IV wherein
R is an alkyl group containing from 6 to 18 carbon atoms, a cycloalkyl group containing from 5 to 7 carbon atoms, benzyl, benzyl substituted by one or two substituents selected from the group consisting of halogen, hydroxy, lower-alkyl lower-alkoxy, nitro, cyano and trifluoromethyl or phenyl substituted by methylenedioxy or one or two substituents selected from the group consisting of halogen, lower-alkyl, lower-alkoxy, nitro, cyano and trifluoromethyl;
Y is an alkylene group containing from 4 to 18 carbon atoms and separating the two 4-(R-NH)-1-pyridinyl groups by from 4 to 18 carbon atoms;
A is a pharmaceutically acceptable anion;
m is 1 or 3;
n is 1 or 2;
x is 1, 2 or 3; and
$(m)(2) = (n)(x)$;

(B) from about 0.75% to about 30% by weight of one or more polyethylene glycol ester surfactants having the structural formulas

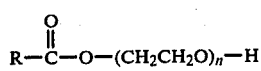
Formula V

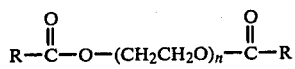
Formula VI

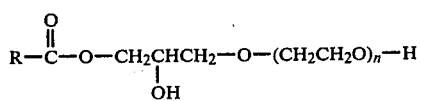
Formula VII wherein R is alkyl or alkenyl having from about 8 to about 20 carbon atoms or lanolin and n is an integer from about 8 to about 200;

(C) from about 0.5% to about 30% by weight of one or more surfactants selected from
(a) betaines having the structural formulas

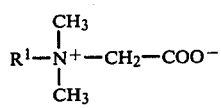
Formula VIII

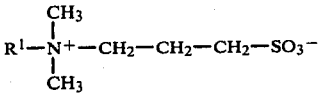
Formula IX

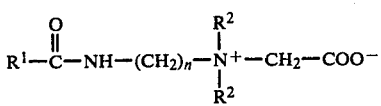
Formula X

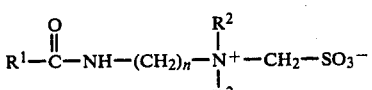
Formula XI

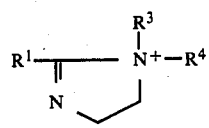
Formula XII wherein $R^1$ is alkyl or alkenyl having from about 8 to about 18 carbon atoms; $R^2$ is methyl, ethyl or 2-hydroxyethyl; $R^3$ is 2-hydroxyethyl or $CH_2COO^-$; $R^4$ is $CH_2COO^-$ or $CH_2CH_2-O-CH_2COO^-$; and n is 2 or 3; and (b) amine oxides having the structural formula

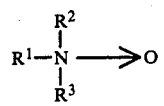
Formula XIII wherein $R^1$ taken alone is methyl, ethyl or 2-hydroxyethyl; $R^2$ taken alone is methyl, ethyl or 2-hydroxyethyl; $R^1$ and $R^2$ taken together are morpholino; $R^3$ is alkyl having from about 8 to about 18 carbon atoms or $R^4CONH(CH_2)_3$ wherein $R^4$ is alkyl having from about 8 to about 18 carbon atoms, and wherein 2-hydroxyethyl can be condensed with from 1 to about 200 units of ethylene oxide; and (D) water, aqueous ethyl alcohol, aqueous isopropyl alcohol or an aqueous ethyl alcohol-isopropyl alcohol mixture.

The preferred amount of antimicrobial agent in the composition is from about 0.01% to about 10% by weight of the composition.

In a process aspect the invention is the process of reducing the number of microbes on living skin which comprises applying to the skin an antimicrobially effective amount of a composition consisting essentially of (A) from about 0.01% to about 10% by weight of one or more antimicrobial agents selected from the group consisting of
(a) a compound of Formula I,
(b) a compound of Formula II or Formula III,
(c) a compound of Formula IV;

(B) from about 0.75% to about 30% by weight of one or more polyethylene glycol ester surfactants of Formula V, Formula VI and Formula VII;

(C) from about 0.5% to about 30% by weight of one or more surfactants selected from
(a) betaines of Formula VIII, Formula IX, Formula X, Formula XI and Formula XII; and
(b) amine oxides of Formula XIII; and (D) water, aqueous ethyl alcohol, aqueous isopropyl alcohol or an aqueous ethyl alcohol-isopropyl alcohol mixture.

In a broader composition of matter aspect the invention is an antimicrobial skin cleansing composition consisting essentially of
(A) an antimicrobially effective amount of a basic amino or ammonium antimicrobial agent;
(B) from about 0.75% to about 30% by weight of one or more polyethylene glycol ester surfactants of Formula V, Formula VI and Formula VIII;
(C) from about 0.5% to about 30% by weight of one or more surfactants selected from
(a) betaines of Formula VIII, Formula IX, Formula X, Formula XI and Formula XII; and
(b) amine oxides of Formula XIII; and
(D) water, aqueous ethyl alcohol, aqueous isopropyl alcohol or an aqueous ethyl alcohol-isopropyl alcohol mixture.

The preferred amount of antimicrobial agent in the composition is from about 0.01% to about 10% by weight of the composition.

In a broader process aspect the invention is the method of reducing the number of microbes on living skin which comprises applying to the skin an antimicrobially effective amount of a composition consisting essentially of
(A) from about 0.01% to about 10% by weight of a basic amino or ammonium antimicrobial agent;
(B) from about 0.75% to about 30% by weight of one or more polyethylene glycol ester surfactants of Formula V, Formula VI and Formula VII;
(C) from about 0.5% to about 30% by weight of one or more surfactants selected from
(a) betaines of Formula VIII, Formula IX, Formula X, Formula XI and Formula XII; and
(b) amine oxides of Formula XIII; and
(D) water, aqueous ethyl alcohol, aqueous isopropyl alcohol or an aqueous ethyl alcohol-isopropyl alcohol mixture.

DETAILED DESCRIPTION OF THE INVENTION INCLUSIVE OF THE PREFERRED EMBODIMENTS

Compositions

The essential ingredients of the compositions are generally and, in most instances, particularly described by the prior art cited above. The compositions are prepared by conventional pharmaceutical methods and in addition to the essential ingredients may also include pharmaceutical adjuncts, for example, emollients, lubricants, stabilizers, dyes, perfumes and preservatives. It spite of the presence of the antimicrobial agent, a preservative may be necessary to prevent growth of microorganisms in the compositions. A pharmaceutically acceptable acid or base may also be added for pH adjustment.

Particularly preferred bisbiguanides are the following compounds of Formula I.

| Compound of Formula | R | R' | n |
|---|---|---|---|
| Ia | p-ClC$_6$H$_5$ | H | 6 |
| Ib |  | H | 6 |

-continued

| Compound of Formula | R | R' | n |
|---|---|---|---|
| Ic | CH$_3$(CH$_2$)$_3$CH(CH$_2$CH$_3$)CH$_2$ | H | 6 |
| Id | CH$_3$(CH$_2$)$_6$ | H | 6 |

The compound of Formula Ia is chlorhexidine (The Merck Index, ibid., monograph 2060). The compound of Formula Ic is alexidine (ibid., monograph 224). The digluconate salt (chlorhexidine gluconate) is a particularly preferred bisbiguanide salt.

A particularly preferred quaternary ammonium salt is benzalkonium chloride (ibid., monograph 1059; R is tetradecyl) (Roccal MC-14 Dihydrate:McCutcheon's Detergents and Emulsifiers, ibid., p. 214), which has the structural formula

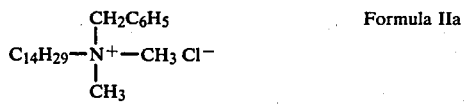

Formula IIa

The following bispyridines of Formula IV are particularly preferred.

| Compound of Formula | R | Y | A | m | n | x |
|---|---|---|---|---|---|---|
| IVa | CH$_3$(CH$_2$)$_6$ | (CH$_2$)$_{12}$ | Cl or Br | 1 | 2 | 1 |
| IVb | CH$_3$(CH$_2$)$_7$ | (CH$_2$)$_{10}$ | Cl or Br | 1 | 2 | 1 |
| IVc | CH$_3$(CH$_2$)$_3$CHCH$_2$<br>                \|<br>              CH$_2$CH$_3$ | (CH$_2$)$_{12}$ | Cl or Br | 1 | 2 | 1 |

Although any polyethylene glycol ester surfactant of Formula V, Formula VI or Formula VII and any betaine surfactant of Formula VIII, Formula IX, Formula X or Formula XI and any amine oxide surfactant of Formula XII can be used in carrying out this invention, specific members of each class may show advantages in specific application areas. Some that have been commercialized only recently are not listed in the current editions of CTFA Cosmetic Ingredient Dictionary (ibid.) or McCutcheon's Detergents & Emulsifiers (ibid.).

Particularly preferred polyethylene glycol ester surfactants are tabulated below.

| Generic Name | CTFA Cosmetic Ingredient Dictionary Page |
|---|---|
| PEG-150 Laurate | 219 |
| PEG-150 Distearate | 211 |
| PEG-78 Glyceryl Cocoate (Cf. PEG-7 Glyceryl Cocoate) | 212 |
| PEG-30 Glyceryl Cocoate (Cf. PEG-7 Glyceryl Cocoate) | 212 |

PEG-150 Laurate is the compound of Formula V wherein R is undecyl and n has an average value of 150. PEG-150 Distearate is the compound of Formula VI wherein R is heptadecyl and n has an average value of 150. PEG-78 Glyceryl Cocoate is the compound of Formula VII wherein

represents the coconut acid radical and n has an average value of 78. PEG-30 Glyceryl Cocoate is the compound of Formula VII wherein

represents the coconut acid radical and n has an average value of 30.

Particularly preferred betaine surfactants are tabulated below.

| Generic Name | Type | CTFA Cosmetic Ingredient Dictionary Page |
|---|---|---|
| Coco-betaine | Formula VIII | 67 |
| Coco-sultaine | Formula IX | 68 |
| Cocamidopropyl Betaine | Formula X | 65 |
| Cocamidopropyl Sultaine | Formula XI | 66 |
| Amphoteric-1 | Formula XII | 24 |

Coco-betaine is the compound of Formula VIII wherein $R^1$ represents the coconut radical. Coco-sultaine is the compound of Formula IX wherein $R^1$ represents the coconut radical. Cocamidopropyl Betaine is the compound of Formula X wherein n is 3,

represents the coconut acid radical and $R^2$ is methyl. Cocamidopropyl Sultaine is the compound of Formula XI wherein n is 3,

represents the coconut acid radical and $R^2$ is methyl. Amphoteric-1 is the compound of Formula XII wherein $R^1$ represents the coconut radical, $R^3$ is 2-hydroxyethyl and $R^4$ is $CH_2COO^-$.

Particularly preferred amine oxide surfactants are tabulated below.

| Generic Name | CTFA Cosmetic Ingredient Dictionary Page |
|---|---|
| Myristamine Oxide | 179 |
| Coco-morpholine Oxide | 67 |
| Cocamidopropylamine Oxide | 65 |
| Dihydroxyethyl Cocamine Oxide | 95 |

Myristamine Oxide is the compound of Formula XIII wherein $R^1$ is methyl, $R^2$ is methyl and $R^3$ is tetradecyl. Coco-morpholine Oxide is the compound of Formula XIII wherein $R^1$ and $R^2$ taken together are morpholino and $R^3$ represents the coconut radical. Cocamidopropylamine Oxide is the compound of Formula I wherein $R^1$ is methyl, $R^2$ is methyl and $R^3$ is $R^4CONH(CH_2)_3$ wherein $R^4CO$ represents the coconut acid radical. Dihydroxyethyl Cocamine Oxide is the compound of Formula XIII wherein $R^1$ is 2-hydroxyethyl, $R^2$ is 2-hydroxyethyl and $R^3$ is the coconut radical.

Compatibility

Compatability of the antimicrobial agents of Formula Id, Formula IIa, Formula IVa (A=Br), Formula IVb (A=Br) and Formula IVc (A=Br) with a prototype vehicle of the invention was tested by a serial dilution test against Staphylococcus aureus ATCC 6538. Volumes of two milliliters were used. Dilutions were in tryptose-phosphate broth. Incubation was for 16–18 hours at 37° C. Growth was verified with 2,3,5-triphenyltetrazolium chloride. The inoculum was $1.8 \times 10^5$ viable cells per tube. There follows the formula of the prototype vehicle.

| Ingredient | Percent by Weight |
|---|---|
| PEG-150 Laurate | 12.0 |
| Isopropyl Alcohol* | 3.22 |
| Cocamidopropyl Betaine | 3.00 |
| Laneth-16 | 1.00 |
| Edetate Disodium | 0.500 |
| PEG-150 Distearate | 0.500 |
| PEG-2M | 0.100 |
| Perfume | 0.100 |
| FD&C Blue No. 1 | 0.000800 |
| FD&C Yellow No. 5 | 0.000320 |
| Gluconic Acid or Sodium Hydroxide to make | pH about 5.5 |
| Purified Water to make | 100.0 |

Laneth-16 is the polyethylene glycol ether of Lanolin Alcohol with an average ethoxylation value of 16. PEG-2M is the polymer of ethylene oxide having the structural formula $H(OCH_2CH_2)_nOH$ wherein n has an average value of 2000.
*To make 4% by volume The following results were obtained.

| Added Vehicle ($\mu$g/ml) | Minimum Inhibitory Concentration (MIC) ($\mu$g/ml) of Compound of Formula | | | | |
|---|---|---|---|---|---|
| | Id+ | IIa | IVa° | IVb° | IVc° |
| 0 | 0.25 | 0.5 | 0.39 | 0.5 | 0.25 |
| 15.6 | 0.25 | 0.5 | 0.195 | 0.5 | 0.25 |
| 31.2 | 0.25 | 0.5 | 0.39 | 0.5 | 0.25 |
| 62.5 | 0.25 | 0.5 | 0.39 | 0.5 | 0.25 |
| 125.0 | 0.25 | 0.5 | 0.10 | 0.5 | 0.125 |
| 250.0 | 0.25 | 0.5 | 0.10 | 0.25 | 0.0625 |
| 500.0 | 0.25 | 0.5 | 0.10 | 0.125 | 0.125 |
| 1000.0 | 0.25 | 1.0 | 0.195 | 0.125 | 0.125 |
| 2000.0 | 0.50 | 1.0 | 0.10 | 0.125 | 0.125 |
| 4000.0 | 0.50 | 1.95 | 0.195 | 0.25 | 0.25 |
| 8000.0 | 0.50 | 1.95 | 0.10 | 0.25 | 0.25 |
| 16000.0 | * | * | * | * | * |
| 32000.0 | ** | ** | ** | ** | ** |
| 64000.0 | ** | ** | ** | ** | ** |

+Expressed as free base
°Expressed as cation
*MIC of vehicle alone
**No growth at this concentration of vehicle It was concluded that each of the five antimicrobial agents tested was compatible with the prototype vehicle.

EXAMPLES

The following examples still more particularly describe the compositions of the invention.

EXAMPLE 1

| Ingredient | Percent by Weight |
|---|---|
| Chlorhexidine Gluconate | 4.00 |
| PEG-78 Glyceryl Cocoate | 10.0 |

-continued

| Ingredient | Percent by Weight |
|---|---|
| Amphoteric-1 | 5.00 |
| Laneth-16 | 1.00 |
| Benzyl Alcohol | 1.00 |
| Acetamide MEA | 0.750 |
| PEG-30 Glyceryl Cocoate | 0.500 |
| Color | 0.00100 |
| Perfume | 0.0500 |
| Gluconic Acid to make pH about 5.5, about | 2.19 |
| Purified Water to make | 100.0 |

Acetamide MEA is N—(2-hydroxyethyl)acetamide.

EXAMPLE 2

| Ingredient | Percent by Weight |
|---|---|
| Compound of Formula IVb (A = Cl) | 2.00 |
| PEG-150 Laurate | 12.0 |
| Isopropyl Alcohol | 3.22 |
| Cocamidopropyl Betaine | 5.00 |
| Laneth-16 | 1.00 |
| Edetate Disodium | 0.500 |
| PEG-150 Distearate | 0.500 |
| PEG-2M | 0.100 |
| Perfume | 0.100 |
| Color | 0.00100 |
| Sodium Hydroxide to make pH about 5.5 | 0.023 |
| Purified Water to make | 100.00 |

EXAMPLE 3

| Ingredient | Percent by Weight |
|---|---|
| Compound of Formula IVb (A = Cl) | 2.00 |
| PEG-78 Glyceryl Cocoate | 10.0 |
| Dihydroxyethyl Cocoamine Oxide | 5.00 |
| Citric Acid | 0.384 |
| Sodium Hydroxide to make pH about 5.5 | — |
| Purified Water to make | 100.00 |

EXAMPLE 4

| Ingredient | Percent by Weight |
|---|---|
| Chlorhexidine Gluconate | 4.00 |
| Amphoteric-1 | 2.50 |
| Cocamidopropylamine Oxide | 2.00 |
| PEG-78 Glyceryl Cocoate | 10.0 |
| PEG-30 Glyceryl Cocoate | 0.500 |
| Laneth-16 | 1.00 |
| Acetamide MEA | 0.750 |
| Color | 0.00100 |
| Perfume | 0.0500 |
| Gluconic Acid or Sodium Hydroxide to make pH about 5.5 | — |
| Acetic Acid | 0.500 |
| Benzyl Alcohol | 1.00 |
| Purified Water to make | 100.00 |

EXAMPLE 5

| Ingredient | Percent by Weight |
|---|---|
| Chlorhexidine Gluconate | 4.00 |
| Dihydroxyethyl Cocamine Oxide | 3.00 |
| PEG-150 Distearate | 0.750 |
| Laneth-16 | 1.00 |
| Benzyl Alcohol | 2.00 |

-continued

| Ingredient | Percent by Weight |
|---|---|
| Perfume | 0.100 |
| Color | 0.00100 |
| Gluconic Acid or Sodium Hydroxide to make pH about 5.5 | — |
| Purified Water to make | 100.00 |

Method of Use

The composition of Example 2 was tested for antimicrobial effect on human hands using a gloved-hand model (R. N. Michaud, M. B. McGrath and W. A. Goss, Journal of Clinical Microbiology, vol. 3, 1976, pp. 406–413). Twelve hands were randomly assigned for washes with the composition of Example 2, and twelve hands were randomly assigned for washes with a corresponding composition differing only by absence of the antimicrobial agent (control). Each hand was washed four times within six hours with a minimum of one hour between washes using five milliliters of each composition for each wash. During each wash the opposite hand of each person was protected with a surgical glove.

Microbiological samples for quantitative determination of aerobic resident bacteria were obtained from each hand immediately prior to the first wash (Wash 1 Pre), after a glove-wearing period of one hour subsequent to the first (Wash 1 $T_1$), second (Wash 2 $T_1$) and fourth (Wash 4 $T_1$) washes, and after a non-glove-wearing period of twenty hours after the fourth wash (Wash 4 $T_{20}$). Total bacterial counts per hand were expressed as logarithms to the base 10. The hand-degerming effect after one wash was evaluated as the bacterial reduction (Wash 1 Pre-Wash 1 $T_1$), abbreviated ($W_1$Pre-$W_1T_1$). Cumulative effects after two washes and four washes were evaluated as the bacterial reductions (Wash 1 Pre-Wash 2 $T_1$), abbreviated ($W_1$Pre-$W_2T_1$), and (Wash 1 Pre-Wash 4 $T_1$), abbreviated ($W_1$Pre-$W_4T_1$). Persistent effect was evaluated as the bacterial reduction (Wash 1 Pre-Wash 4 $T_{20}$), abbreviated ($W_1$Pre-$W_4T_{20}$).

Microbiological samples were taken by extracting each gloved hand with sampling fluid (100 ml. of 0.1% Triton X-100 in 0.074 M phosphate buffer at pH 7.8±0.1). An aliquot (10 ml.) of each extract was mixed with chilled neutralizer (10 ml. of 0.0003 M potassium dihydrogen phosphate buffer of pH 7.2 containing 2% Tamol N Micro brand of sodium salt of condensed naphthalene sulfonic acid anionic dispersant). Decimal dilutions ($10^{-1}$, $10^{-2}$, $10^{-3}$) of the neutralized aliquot were prepared in 0.0003 M $KH_2PO_4$ buffer, pH 7.2, and were plated in triplicate with trypticase soy agar using the pour-plate technique. Plates were incubated aerobically at 30°±2° C. for 48–72 hours. A total colony count for each plate was determined using an automated colony counter. Average colony counts were used to estimate the total number of bacteria recovered per hand.

The following results were obtained

| Sample | Mean (n = 12) $Log_{10}$ Control | Number of Bacteria Recovered Per Hand Example 2 |
|---|---|---|
| Wash 1 Pre | 6.372 | 6.165 |
| Wash 1 $T_1$ | 6.537 | 5.770 |
| Wash 2 $T_1$ | 6.316 | 5.030 |
| Wash 4 $T_1$ | 5.978 | 4.296 |
| Wash 4 $T_{20}$ | 5.846 | 4.867 |

-continued

| Difference | Mean (n = 12) Log$_{10}$ Control | Bacterial Reductions Per Hand Example 2 |
|---|---|---|
| W$_1$Pre − W$_1$T$_1$ | −0.166 | 0.394 |
| W$_1$Pre − W$_2$T$_1$ | 0.055 | 1.135 |
| W$_1$Pre − W$_4$T$_1$ | 0.393 | 1.869 |
| W$_1$Pre − W$_4$T$_{20}$ | 0.525 | 1.297 |

The foregoing mean log$_{10}$ bacterial reductions were significantly greater (P≦0.01) for the hands treated with the composition of Example 2 than for the hands treated with the control composition.

Opacified Compositions

The foregoing examples of the compositions aspect of the invention are clear as contrasted with opaque. By addition of appropriate ingredients compositions according to the invention can be opacified and emulsified as illustrated by the following examples.

EXAMPLE 6

| Ingredient | Percent by Weight |
|---|---|
| Chlorhexidine Gluconate | 1.00 |
| PEG-78 Glyceryl Cocoate | 10.0 |
| EMPIGEN OB (Tertiary Alkylamine Oxide 30%) | 10.0 |
| White Soft Paraffin | 6.0 |
| Dihydroxyethyl Cocamine Oxide | 5.26 |
| Acetamide MEA (75%) | 1.0 |
| Benzyl Alcohol | 1.0 |
| Polysorbate 60 | 1.0 |
| Sorbitan Stearate | 1.00 |
| Gluconic Acid to make pH 5.8 | — |
| Purified Water to make | 100.0 |

Polysobate 60 is a mixture of stearate esters of sorbitol and sorbitol anhydrides, consisting predominantly of the monoester, condensed with approximately 20 moles of ethylene oxide. Sorbitan Stearate is the monoester of stearic and hexitol anhydrides derived from sorbitol.

EXAMPLE 7 is the same as Example 6 except tht the percent by weight of chlorhexidine gluconate is increased to 4.00.

Comparative Sudsing Test and Sudsing Attribute Evaluation

In order to show that the presently described and claimed invention achieves its above-stated objective to provide antimicrobial skin cleansing compositions having better sudsing ability than the compositions of the prior art, the following comparative in vitro sudsing test and in vivo sudsing attribute evaluation were conducted.

In Vitro Sudsing Test

The compositions compared in this test were the composition of Example 1 of the present specification, the composition of Example 1 of the present specification excluding chlorhexidine gluconate, and Hibiclens, which is a commercial polyoxyethylene-polyoxypropylene block copolymer antimicrobial skin cleansing composition containing chlorhexidine gluconate and which is considered to be the composition described by EXAMPLE 1 of above-cited U.S. Pat. No. 3,855,140. The composition of Example 1 of the present specification excluding chlorhexidine gluconate was tested in this test in order to show that the absence of the chlorhexidine gluconate does not significantly affect sudsability. This was necessary because, without approval by the United States Food and Drug Administration and due to the presence of the chlorhexidine gluconate, the composition of Example 1 of the present specification could not be evaluated in the in vivo sudsing attribute evaluation described below, which was conducted in humans.

The test composition (0.25 g.) was diluted to 100 ml. with artificially hardened water (0.3 g. calcium chloride in 1 l. of distilled water) in a 250 ml. stoppered graduate cylinder. Lanolin oil (0.05 g.) was added to simulate the natural oil of human hands. The cylinder was rotated end over end at a constant rate and the foam volume was read after 25, 50, 75 and 100 rotations. Five cylinders were used for each composition. The mean foam volumes and standard deviations for each composition were calculated, affording the following results:

| Number of Rotations | Foam Volume (ml.) | | | |
|---|---|---|---|---|
|  | 25 | 50 | 75 | 100 |
| Example 1 | 132 ± 4.5 | 142 ± 7.7 | 164 ± 10.5 | 173 ± 6.6 |
| Example 1 without Chlorhexidine Gluconate | 127 ± 6.0 | 135 ± 10.9 | 149 ± 13.7 | 162 ± 22.3 |
| Hibiclens | 107 ± 2.3 | 111 ± 2.6 | 115 ± 2.6 | 120 ± 3.8 |

The means for Example 1 with or without chlorhexidine gluconate are significantly different from the means for Hibiclens (P<0.01). The means for Example 1 with chlorhexidine gluconate are not significantly different from the means for Example 1 without chlorhexidine gluconate (P<0.1).

In Vivo Sudsing Attribute Evaluation

Since Hibiclens is red in color and the preferred color of the composition of Example 1 of the present specification is green, both a red formulation and a green formulation according to Example 1 (Both lacking chlorhexidine gluconate) were tested. The results were not significantly affected by the difference in color.

Ten persons participated in the evaluation. Each person was instructed to: (1) wash his or her hands with soap and water, (2) rinse the hands and leave them wet, (3) apply one teaspoonful of the skin cleansing compositions to the hands, (4) wash the hands with the skin cleanser for one full minute, adding water as desired, (5) rinse the hands, (6) dry the hands with a towel and (7) repeat steps (1) through (6) three times allowing at least one hour between repetitions.

Each person was instructed to evaluate the skin cleansing composition with regard to four criteria relating to sudsing and to assign one of five values to each criterion as follows: Criteria: initial or flash foam, foam quantity, foam texture, foam stability. Criterion values: poor, fair, mediocre, good, excellent.

The five criterion values were assigned the following numerical values: poor, 0; fair, 25; mediocre, 50; good, 75; excellent, 100. The criterion values for each criterion were averaged and gave the following results:

| Criterion | Criterion Value | | |
|---|---|---|---|
|  | Example 1 Without Chlorhexidine Gluconate (Green) | Example 1 Without Chlorhexidine Gluconate (Red) | Hibiclens (Red) |
| Initial or | 78 ± 8 | 78 ± 8 | 23 ± 28 |

| | Criterion Value | | |
|---|---|---|---|
| Criterion | Example 1 Without Chlorhexidine Gluconate (Green) | Example 1 Without Chlorhexidine Gluconate (Red) | Hibiclens (Red) |
| Flash Foam | | | |
| Foam Quantity | 85 ± 13 | 78 ± 8 | 35 ± 32 |
| Foam Texture | 83 ± 17 | 80 ± 11 | 35 ± 32 |
| Foam Stability | 83 ± 17 | 78 ± 8 | 38 ± 34 |

All of the criterion values for Example 1 without chlorhexidine gluconate are significantly different from those of Hibiclens (P<0.01).

We claim:

1. An antimicrobial skin cleansing composition consisting essentially of (A) an antimicrobially effective amount of one or more antimicrobial agents selected from the group consisting of (a) a compound having the structural formula

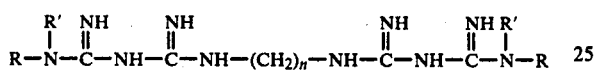

wherein R taken alone is phenyl substituted by alkyl, alkoxy, nitro or halo, p-(2,2-dichlorocyclopropyl)phenyl, alkyl having from 6 to 16 carbon atoms, cycloalkyl or polycyclic alkyl having more than 6 carbon atoms or lower-alkyl-cycloalkyl or cycloalkyl-lower-alkyl having from 1 to 4 carbons in lower alkyl; R' taken alone is hydrogen; R and R' taken together are 3-azabicyclo(3,2,2)nonyl; and n is an integer from 3 to 9; or a pharmaceutically acceptable salt thereof;

(b) a compound having the structural formula

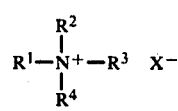

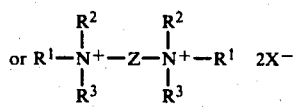

wherein $R^1$ is long-chain alkyl or aralkyl; $R^2$ is short-chain alkyl, long-chain alkyl or aralkyl, benzyl or part of an aromatic system or non-aromatic system; $R^3$ and $R^4$ are short-chain alkyl or part of an aromatic ring system or non-aromatic ring system; Z is a carbon-hydrogen chain; and X is a pharmaceutically acceptable anion; and (c) a compound having the structural formula

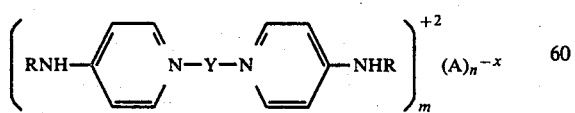

wherein

R is an alkyl group containing from 6 to 18 carbon atoms, a cycloalkyl group containing from 5 to 7 carbon atoms, benzyl, benzyl substituted by one or two substituents selected from the group consisting of halogen, hydroxy, lower-alkyl, lower-alkoxy, nitro, cyano and trifluoromethyl or phenyl substituted by methylenedioxy or one or two substituents selected from the group consisting of halogen, lower-alkyl, lower-alkoxy, nitro, cyano and trifluoromethyl;

Y is an alkylene group containing from 4 to 18 carbon atoms and separating the two 4-(R-NH)-1-pyridinyl groups by from 4 to 18 carbon atoms;

A is a pharmaceutically acceptable anion;

m is 1 or 3;

n is 1 or 2;

x is 1, 2 or 3; and (m)(2)=(n)(x);

(B) from about 0.75% to about 30% by weight of one or more polyethylene glycol ester surfactants having the structural formulas

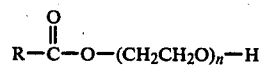

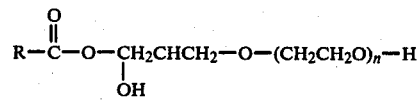

wherein R is alkyl or alkenyl having from about 8 to about 20 carbon atoms or lanolin and n is an integer from about 8 to about 200;

(C) from about 0.5% to about 30% by weight of one or more surfactants selected from the group consisting of (a) betaines having the structural formulas

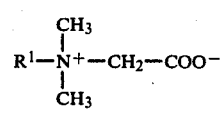

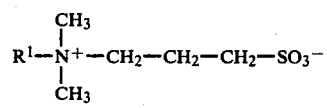

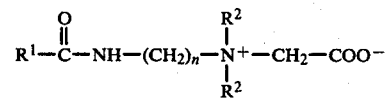

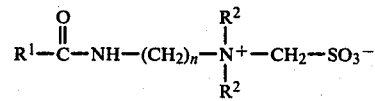

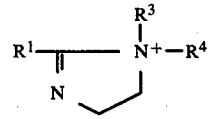

wherein $R^1$ is alkyl or alkenyl having from about 8 to about 18 carbon atoms; $R^2$ is methyl, ethyl or 2-hydroxyethyl; $R^3$ is 2-hydroxyethyl or $CH_2COO^-$; $R^4$ is $CH_2COO^-$ or $CH_2CH_2$-O-$CH_2COO^-$; an n is 2 or 3; and (b) amine oxides having the structural formula $$R^1-\underset{R^3}{\underset{|}{N}}\overset{R^2}{\overset{|}{\longrightarrow}}O$$

wherein $R^1$ taken alone is methyl, ethyl or 2-hydroxyethyl; $R^2$ taken alone is methyl, ethyl or 2-hydroxyethyl; $R^1$ and $R^2$ taken together are morpholino; $R^3$ is alkyl having from about 8 to about 18 carbon atoms or $R^4CONH(CH_2)_3$ wherein $R^4$ is alkyl having from about 8 to about 18 carbon atoms; and wherein 2-hydroxyethyl can be condensed with from 1 to about 200 units of ethylene oxide; and (D) water, aqueous ethyl alcohol, aqueous isopropyl alcohol or an aqueous ethyl alcohol-isopropyl alcohol mixture.

2. A composition according to claim 1 wherein the amount of antimicrobial agent is from about 0.01% to about 10% by weight of the composition.

3. The process of reducing the number of microbes on living skin which comprises applying to the skin an antimicrobially effective amount of a composition according to claim 2.

4. An antimicrobial skin cleansing composition consisting essentially of (A) an antimicrobially effective amount of one or more antimicrobial agents selected from the group consisting of a compound having the structural formula $$R-\underset{R'}{\underset{|}{N}}-\overset{NH}{\overset{||}{C}}-NH-\overset{NH}{\overset{||}{C}}-NH-(CH_2)_n-NH-\overset{NH}{\overset{||}{C}}-NH-\overset{NHR'}{\overset{||}{C}}-\underset{R}{\underset{|}{N}}-R$$

wherein R taken alone is phenyl substituted by alkyl, alkoxy, nitro or halo, p-(2,2-dichlorocyclopropyl)-phenyl, alkyl having from 6 to 16 carbon atoms, cycloalkyl or polycyclic alkyl having more than 6 carbon atoms or lower-alkyl-cycloalkyl or cycloalkyl-lower-alkyl having from 1 to 4 carbons in lower alkyl; R' taken alone is hydrogen; R and R' taken together are 3-azabicyclo(3,2,2)nonyl; and n is an integer from 3 to 9; or a pharmaceutically acceptable salt thereof;

(B) from about 0.75% to about 30% by weight of one or more polyethylene glycol ester surfactants having the structural formulas $$R-\overset{O}{\overset{||}{C}}-O-(CH_2CH_2O)_n-H$$

$$R-\overset{O}{\overset{||}{C}}-O-(CH_2CH_2O)_n-\overset{O}{\overset{||}{C}}-R$$

$$R-\overset{O}{\overset{||}{C}}-O-CH_2\underset{OH}{\underset{|}{CH}}CH_2-O-(CH_2CH_2O)_n-H$$

wherein R is alkyl or alkenyl having from about 8 to about 20 carbon atoms or lanolin and n is an integer from about 8 to about 200;

(C) from about 0.5% to about 30% by weight of one or more surfactants selected from the group consisting of (a) betaines having the structural formulas $$R^1-\underset{CH_3}{\underset{|}{N^+}}-CH_2-COO^-$$
$$\phantom{R^1-N^+-}CH_3$$

$$R^1-\underset{CH_3}{\underset{|}{N^+}}-CH_2-CH_2-CH_2-SO_3^-$$
$$\phantom{R^1-N^+-}CH_3$$

$$R^1-\overset{O}{\overset{||}{C}}-NH-(CH_2)_n-\underset{R^2}{\underset{|}{N^+}}-CH_2-COO^-$$

$$R^1-\overset{O}{\overset{||}{C}}-NH-(CH_2)_n-\underset{R^2}{\underset{|}{N^+}}-CH_2-SO_3^-$$

$$R^1-\underset{N}{\overset{R^3}{\overset{|}{\boxed{\phantom{xx}}}}}N^+-R^4$$

wherein $R^1$ is alkyl or alkenyl having from about 8 to about 18 carbon atoms; $R^2$ is methyl, ethyl or 2-hydroxyethyl; $R^3$ is 2-hydroxyethyl or $CH_2COO^-$; $R^4$ is $CH_2COO^-$ or $CH_2CH_2-O-CH_2COO^-$; and n is 2 or 3; and (b) amine oxides having the structural formula $$R^1-\underset{R^3}{\underset{|}{N}}\overset{R^2}{\overset{|}{\longrightarrow}}O$$

wherein $R^1$ taken alone is methyl, ethyl or 2-hydroxyethyl; $R^2$ taken alone is methyl, ethyl or 2-hydroxyethyl; $R^1$ and $R^2$ taken together are morpholino; $R^3$ is alkyl having from about 8 to about 18 carbon atoms or $R^4CONH(CH_2)_3$ wherein $R^4$ is alkyl having from about 8 to about 18 carbon atoms, and wherein 2-hydroxyethyl can be condensed with from 1 to about 200 units of ethylene oxide; and (D) water, aqueous ethyl alcohol, aqueous isopropyl alcohol or an aqueous ethyl alcohol-isopropyl alcohol mixture.

5. A composition according to claim 4 wherein the amount of antimicrobial agent is from about 0.01% to about 10% by weight of the composition.

6. The process of reducing the number of microbes on living skin which comprises applying to the skin an antimicrobially effective amount of a composition according to claim 5.

7. A composition according to claim 5 wherein the antimicrobial agent is chlorhexidine or a pharmaceutically acceptable salt thereof.

8. The process of reducing the number of microbes on living skin which comprises applying to the skin an antimicrobially effective amount of a composition according to claim 7.

9. A composition according to claim 7 wherein the salt is the digluconate salt.

10. The process of reducing the number of microbes on living skin which comprises applying to the skin an antimicrobially effective amount of a composition according to claim 9.

11. A composition according to claim 9 wherein the surfactant of part (C) is a betaine.

12. A composition according to claim 11 wherein the betaine has the structural formula

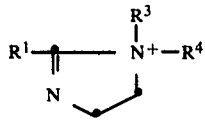

wherein $R^1$ represents the coconut radical, $R^3$ is 2-hydroxyethyl and $R^4$ is $CH_2COO^-$.

13. A composition according to claim 12 which contains two polyethylene glycol ester surfactants of part (B), both having the structural formula

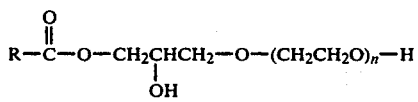

wherein

represents the coconut acid radical, one wherein n has an average value of 78 and the other wherein n has an average value of 30.

14. The process of reducing the number of microbes on living skin which comprises applying to the skin an antimicrobially effective amount of a composition according to claim 11.

15. An antimicrobial skin cleansing composition consisting essentially of (A) an antimicrobially effective amount of one or more antimicrobial agents selected from the group consisting of a compound having the structural formula

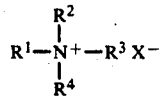

or

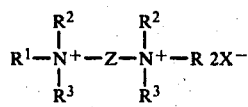

wherein $R^1$ is long-chain alkyl or aralkyl; $R^2$ is short-chain alkyl, long-chain alkyl or aralkyl, benzyl or part of an aromatic system or non-aromatic system; $R^3$ and $R^4$ are short-chain alkyl or part of an aromatic ring system or non-aromatic ring system; Z is a carbon-hydrogen chain; and X is a pharmaceutically acceptable anion;

(B) from about 0.75% to about 30% by weight of one or more polyethylene glycol ester surfactants having the structural formulas

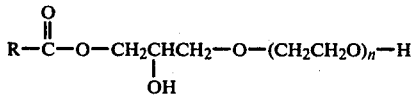

wherein R is alkyl or alkenyl having from about 8 to about 20 carbon atoms or lanolin and n is an integer from about 8 to about 200;

(C) from about 0.5% to about 30% by weight of one or more surfactants selected from the group consisting of (a) betaines having the structural formulas

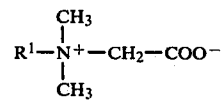

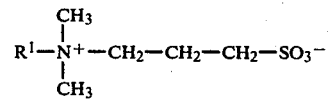

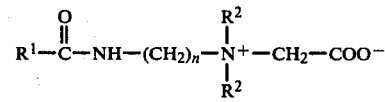

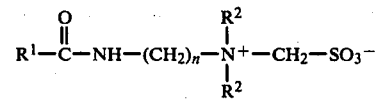

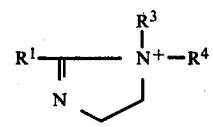

wherein $R^1$ is alkyl or alkenyl having from about 8 to about 18 carbon atoms; $R^2$ is methyl, ethyl or 2-hydroxyethyl; $R^3$ is 3-hydroxyethyl or $CH_2COO^-$; $R^4$ is $CH_2COO^-$ or $CH_2CH_2-O-CH_2COO^-$; and n is 2 or 3; and (b) amine oxides having the structural formula

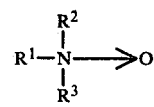

wherein $R^1$ taken alone is methyl, ethyl or 2-hydroxyethyl; $R^2$ taken alone is methyl, ethyl or 2-hydroxyethyl; $R^1$ and $R^2$ taken together are morpholino; $R^3$ is alkyl having from about 8 to about 18 carbon atoms or $R^4CONH(CH_2)_3$ wherein $R^4$ is alkyl having from about 8 to about 18 carbon atoms, and wherein 2-hydroxyethyl can be condensed with from 1 to about 200 units of ethylene oxide; and (D) water, aqueous ethyl alcohol, aqueous isopropyl alcohol or an aqueous ethyl alcohol-isopropyl alcohol mixture.

16. A composition according to claim 15 wherein the amount of antimicrobial agent is from about 0.01% to about 10% by weight of the composition.

17. The process of reducing the number of microbes on living skin which comprises applying to the skin an antimicrobially effective amount of a composition according to claim 16.

18. A composition according to claim 16 wherein the antimicrobial agent is benzalkonium chloride.

19. The process of reducing the number of microbes on living skin which comprises applying to the skin an antimicrobially effective amount of a composition according to claim 18.

20. An antimicrobial skin cleansing composition consisting essentially of
(A) an antimicrobially effective amount of one or more antimicrobial agents selected from the group consisting of a compound having the structural formula

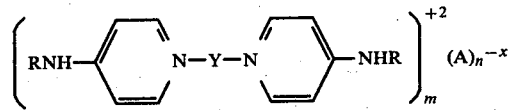

wherein
R is an alkyl group containing from 6 to 18 carbon atoms, a cycloalkyl group containing from 5 to 7 carbon atoms, benzyl, benzyl substituted by one or two substituents selected from the group consisting of halogen, hydroxy, lower-alkyl, lower-alkoxy, nitro, cyano and trifluoromethyl or phenyl substituted by methylenedioxy or one or two substituents selected from the group consisting of halogen, lower-alkyl, lower-alkoxy, nitro, cyano and trifluoromethyl;
Y is an alkylene group containing from 4 to 18 carbon atoms and separating the two 4-(R-NH)-1-pyridinyl groups by from 4 to 18 carbon atoms;
A is a pharmaceutically acceptable anion;
m is 1 or 3;
n is 1 or 2;
x is 1, 2 or 3; and
(m)(2)=(n)(x);
(B) from about 0.75% to about 30% by weight of one or more polyethylene glycol ester surfactants having the structural formulas

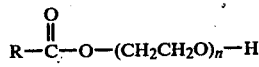

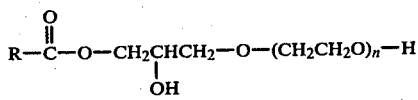

wherein R is alkyl or alkenyl having from about 8 to about 20 carbon atoms or lanolin and n is an integer from about 8 to about 200;

(C) from about 0.5% to about 30% by weight of one or more surfactants selected from the group consisting of
(a) betaines having the structural formulas

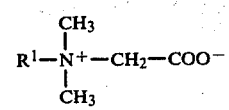

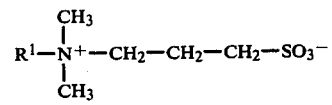

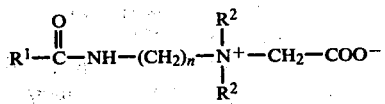

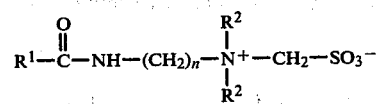

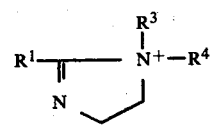

wherein $R^1$ is alkyl or alkenyl having from about 8 to about 18 carbon atoms; $R^2$ is methyl, ethyl or 2-hydroxyethyl; $R^3$ is 2-hydroxyethyl or $CH_2COO^-$; $R^4$ is $CH_2COO^-$ or $CH_2CH_2-O-CH_2COO^-$; and n is 2 or 3; and
(b) amine oxides having the structural formula

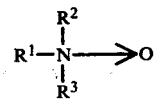

wherein $R^1$ taken alone is methyl, ethyl or 2-hydroxyethyl; $R^2$ taken alone is methyl, ethyl or 2-hydroxyethyl; $R^1$ and $R^2$ taken together are morpholino; $R^3$ is alkyl having from about 8 to about 18 carbon atoms or $R^4CONH(CH_2)_3$ wherein $R^4$ is alkyl having from about 8 to about 18 carbon atoms, and wherein 2-hydroxyethyl can be condensed with from 1 to about 200 units of ethylene oxide; and
(D) water, aqueous ethyl alcohol, aqueous isopropyl alcohol or an aqueous ethyl alcohol-isopropyl alcohol mixture.

21. A composition according to claim 20 wherein the amount of antimicrobial agent is from about 0.01% to about 10% by weight of the composition.

22. The process of reducing the number of microbes on living skin which comprises applying to the skin an antimicrobially effective amount of a composition according to claim 21.

23. A composition according to claim 21 wherein in the structural formula of the antimicrobial agent R is $CH_3(CH_2)_7$, Y is $(CH_2)_{10}$, A is Cl or Br, m is 1, n is 2 and x is 1.

24. The process of reducing the number of microbes on living skin which comprises applying to the skin an antimicrobially effective amount of a composition according to claim 23.

25. A composition according to claim 23 wherein the surfactant of part (C) is a betaine.

26. The process of reducing the number of microbes on living skin which comprises applying to the skin an antimicrobially effective amount of a composition according to claim 25.

27. A composition according to claim 23 wherein the surfactant of part (C) is an amine oxide.

28. A composition according to claim 27 wherein in the amine oxide having the structural formula $$R^1-\underset{\underset{R^3}{|}}{\overset{\overset{R^2}{|}}{N}}\rightarrow O$$

$R^1$ is hydroxyethyl, $R^2$ is hydroxyethyl and $R^3$ is the coconut radical.

29. A composition according to claim 27 wherein the polyethylene glycol surfactant of part (B) has the structural formula $$R-\overset{\overset{O}{\|}}{C}-O-CH_2CHCH_2-O-(CH_2CH_2O)_n-H$$
$$\underset{OH}{|}$$

wherein $$R-\overset{\overset{O}{\|}}{C}$$

represents the coconut acid radical and n has an average value of 78.

30. The process of reducing the number of microbes on living skin which comprises applying to the skin an antimicrobially effective amount of a composition according to claim 27.

31. An antimicrobial skin cleansing composition consisting essentially of (A) an antimicrobially effective amount of chlorhexidine gluconate;

(B) from about 0.75% to about 30% by weight of two polyethylene glycol ester surfactants having the structural formula $$R-\overset{\overset{O}{\|}}{C}-O-CH_2CHCH_2-O-(CH_2CH_2O)_n-H$$
$$\underset{OH}{|}$$

wherein $$R-\overset{\overset{O}{\|}}{C}$$

represents the coconut acid radical, one wherein n has an average value of 78 and the other wherein n has an average value of 30;

(C) from about 0.5% to about 30% by weight of a betaine surfactant having the structural formula $$R^1-\underset{N}{\overset{\|}{\bullet}}\underset{\diagdown\diagup}{\overset{\overset{R^3}{|}}{N^+-R^4}}$$

wherein $R^1$ represents the coconut radical, $R^3$ is 2-hydroxyethyl and $R^4$ is $CH_2COO^-$; and (D) water.

* * * * *